United States Patent [19]

Karpiel

[11] Patent Number: 5,320,602
[45] Date of Patent: Jun. 14, 1994

[54] PEEL-AWAY ENDOSCOPIC RETROGRADE CHOLANGIO PANCREATOGRAPHY CATHETER AND A METHOD FOR USING THE SAME

[75] Inventor: John Karpiel, Winston-Salem, N.C.
[73] Assignee: Wilson-Cook Medical, Inc., Winston-Salem, N.C.
[21] Appl. No.: 61,854
[22] Filed: May 14, 1993
[51] Int. Cl.$^5$ .................... A61M 25/00; A61M 29/00
[52] U.S. Cl. ........................ 604/54; 604/161; 128/4
[58] Field of Search ............... 604/49, 51, 161, 285, 604/101; 128/4, 6, 8

[56] References Cited

U.S. PATENT DOCUMENTS

| Re. 31,855 | 3/1985 | Osborne | 604/161 |
|---|---|---|---|
| 3,382,872 | 5/1968 | Rubin . | |
| 3,550,591 | 12/1970 | MacGregor . | |
| 4,166,469 | 9/1979 | Littleford . | |
| 4,167,939 | 9/1979 | Storz | 604/54 |
| 4,243,050 | 1/1981 | Littleford . | |
| 4,306,562 | 12/1981 | Osborne . | |
| 4,345,606 | 8/1982 | Littleford . | |
| 4,411,654 | 10/1983 | Boarini et al. | 604/165 |
| 4,412,832 | 11/1983 | Kling et al. | 604/161 |
| 4,596,559 | 6/1986 | Ekischhacker | 604/161 |
| 4,631,054 | 12/1986 | Kim | 604/54 |
| 4,747,833 | 5/1988 | Kousai et al. | 604/164 |
| 4,773,394 | 9/1988 | Reichstein | 604/54 |
| 4,776,846 | 10/1988 | Wells | 604/161 |
| 4,781,690 | 11/1988 | Ishida et al. | 604/164 |
| 4,801,294 | 1/1989 | Okada | 604/171 |
| 4,813,929 | 3/1989 | Semrad | 604/51 |
| 4,883,468 | 11/1989 | Kousai et al. | 604/164 |
| 4,983,168 | 1/1991 | Moorhead | 604/161 |
| 4,997,424 | 3/1991 | Little | 604/280 |
| 5,052,998 | 10/1991 | Zimmon | 604/8 |
| 5,078,701 | 1/1992 | Grassi et al. | 604/54 |
| 5,195,978 | 3/1993 | Schiffer | 604/161 |

FOREIGN PATENT DOCUMENTS

WO93/05841 4/1993 PCT Int'l Appl. .

Primary Examiner—John G. Weiss
Attorney, Agent, or Firm—Woodard, Emhardt, Naughton, Moriarty & McNett

[57] ABSTRACT

A peel-away endoscopic retrograde cholangio pancreatography catheter and a method for using the same is provided. An endoscope having a passage therethrough is introduced into the mouth of a patient and is guided through the patent's gastroentral tract until an opening at the distal end of the endoscope is in close proximity with the papilla of vater leading to the common bile and pancreatic ducts. A peel-away ERCP catheter is provided which may be guided through the lumen of the endoscope until the distal tip of the catheter emerges from the opening at the distal end of the endoscope. The distal end of the catheter may be guided through the sphincter of oddi and into the common bile or pancreatic duct. A radiopaque dye may be injected through the catheter, into the duct. Additionally, a guide wire may be guided into the common bile or pancreatic duct through the catheter. Thereafter, the catheter may be easily removed without disturbing the placement of the guide wire by pulling on knobs attached to tabs at the proximal end of the catheter while the proximal end of the guide wire is held in place. The force applied to the catheter tabs causes the catheter to split longitudinally along two longitudinal grooves cut into the body of the catheter. Thus, the catheter peels-away from the guide wire without displacing the guide wire. Simultaneously, the pulling force on the tabs splits the catheter away from the guide wire while pulling the catheter up the guide wire. Additionally, a biliary stent can be pushed into the duct using a second peel-away catheter which may then be removed in accordance with the method of the present invention.

13 Claims, 8 Drawing Sheets

PEEL-AWAY ENDOSCOPIC RETROGRADE CHOLANGIO PANCREATOGRAPHY CATHETER AND A METHOD FOR USING THE SAME

BACKGROUND OF THE INVENTION

This invention relates to a splittable or peel-away ERCP catheter and more particularly to a method of using a peel-away ERCP catheter the distal end of which has been inserted into the common bile or pancreatic duct via an endoscope which has been guided through the esophagus and stomach and into the duodenum of a patient.

In certain medical applications it is useful to provide a sheath or catheter that is longitudinally splittable for ease of removal from the human body. For example, the use of a splittable catheter permits the removal of a catheter after a guide wire or other material has been placed therethrough without disturbing the guide wire. Various splittable sheaths and catheters exist which have been designed to split longitudinally along the body to peel-away from a catheter, guide wire or other inserted material.

U.S. Pat. No. 4,776,846 to Wells discloses an apparatus and method for preparing a catheter tube which has a longitudinal line of weakness extending axially therealong is a place for preferential splitting. The method includes co-extruding two materials into the tubular cross-sectional shape. One of the materials forms a surface line along the other which extends readily to a level where the thickness of the tubing cross-section thereat is less. When the co-extruded extra material is removed, a grove is in the surface of the tube, which groove permits easy tearing there along.

U.S. Pat. No. 4,983,168 to Moorehead discloses a layered peel-away hollow sheath, for temporarily creating a passageway into a desired body site of a medical patient for placement of one end of an indwelling device at the body site the sheath. The sheath wall comprise at least two layers, the inside layer being cylindrical and the outside layer comprising two semi-cylindrical segments defining opposed axially directed slits or slots therebetween which comprises tear lines such that the sheath manually tears axially along the single layer tear lines into two pieces for removal of the sheath from around the indwelling device.

U.S. Pat. No. 4,801,294 to Okada discloses a catheter for nasogastric intubation comprising a plastic sheath tube and a fixing means of said tube at nose, said tube having a longitudinal tear-off line over the full length thereof and having elasticity and rigidity slightly larger than those of said catheter, said catheter being inserted in said plastic sheath tube slidably.

U.S. Pat. No. 3,550,591 to McGregor discloses an intravenous catheter unit which provides a needle which can be separated from the catheter after the end of the catheter positioned inside the vein to prevent the needle from tearing or damaging the catheter. The hollow needle is provided with a slit which extends along its entire length. In addition the needle is provided with means of the causing the needle to hinge open to widen the slit enough to pass the catheter therethrough. In this way the needle may be separated from the catheter after the catheter is placed inside the vein.

U.S. Pat. No. 4,781,690 to Oshada, et al. discloses a guiding tube for introducing rodlike medical instruments such as a catheter, which can be easily split and removed. The guiding tube comprises a main body provided with a longitudinal slit and formed of a mixture of first and second materials and a stripe detachably embedded liquid-tight in the slit of the main body and formed of the third material which exhibits a good bonding for the second material but a poor bonding for the first material.

U.S. Pat. No. 4,747,833 to Kousai, et al. discloses a medical instrument-guiding tube for guiding a catheter or other rod-like medical instrument into a blood vessel. This guiding tube comprises a hollow-tube body and at least one linear body integrally joined to the tube body along the longitudinal direction of the tube body. The plastic resin forming the tube body has a poor compatibility with that of the linear body. Tube body and the linear body are engaged together through complimentary concave convex arrangement which can be disengaged with reasonable force.

U.S. Pat. No. 4,883,468 to Kousai, et al. discloses a medical instrument introduction cannula which is useful as a guide means for introducing and indwelling a rod-like material instrument such as a catheter and a guide wire. This cannula is removed after use from the medical instrument by being split. This cannula is formed of a hollow tubular body having a strip member consisting of material different from the other portion of the tubular body, which extends over almost the entire length of the tubular body. The strip member has a weld line along the length of the strip member, or consists of a resin which exhibits a good bonding property only to one of the other components forming the tubular body. The tubular body can be split by way of the weld line or the removal of the strip member having such a bonding property. The method of manufacturing the medical instrument introduction cannula by a two-color extruder is also disclosed.

U.S. Pat. No. 4,997,424 to Little relates to an introducer slitter for slitting an introducer tube portion having, for example, a catheter extending therethrough and into a body vessel while the introducer tube is moved rearwardly relative to the catheter to facilitate separating the introducer from the catheter without having to slide the introducer tube portion over the proximal end of the catheter.

U.S. Pat. No. 5,195,978 to Schiffer discloses a rapid exchange over-the-wire catheter which is provided with one or more breakaway elements for progressively exposing the guide wire from the proximal end toward the distal end of the catheter in a simple and efficient manner. The breakaway element may be formed as a longitudinally aligned pull strip provided in the catheter guide wire lumen or as one or more linearly arrayed tubular breakaway segments in the catheter shaft or as a combination of both features.

U.S. Pat. No. 4,813,929 to Semrad discloses a method and assembly of components for effecting closed chest thoracostomy. A guide wire is removed and a chest tube is introduced through a pleural access catheter, which is split off and removed from the chest tube. FIGS. 5 and 6 of the Semrad reference show a splittable access catheter having knobs that when grasped and pulled in a direction away from the body of the catheter will cause the catheter to split.

U.S. Pat. No. 4,243,050 and 4,345,606 to Littleford disclose an apparatus and related method for implanting pacemaker electrodes and similar devices within a patient including an introducer with a tapered end adapted to extend into the patient's body, and a hollow, tubular sleeve. The sleeve is perforated to form a weakened line. The sleeve may be peeled slightly away at the flange to form tabs which may be used to grasp and peel away the sleeve while removing the same from the vein.

U.S. Pat. No. 4,166,469 to Littleford discloses an apparatus and method for inserting an electrode within a patient with a minimal amount of incision which includes the use of an introducer sleeve which is severed or severable along the length thereof. The introducer sleeve is withdrawn from the patient while the electrode is moving through, severing the sleeve wall along the entire length thereof to enable the removal of the sleeve over the connector plug of the electrode.

U.S. Pat. No. 4,306,562 to Osborne discloses a flexible cannula comprising material which tears readily in a longitudinal direction and thus can be easily removed by pulling tabs on opposite sides of the cannula apart from the catheter or other device that has been inserted into the body. The Osborne cannula readily tears in a longitudinal direction along the length of the structure due to the longitudinal orientation of the material from which it is constructed.

Additionally, it is possible to introduce a standard, non-splittable catheter into the gastroentral tract, via an endoscope, until it is adjacent to the bile duct. However, after a guide wire has been introduced through the catheter, difficulties arise when attempting to remove the catheter. For example, the catheter must be pulled over the entire length of the guide wire by a health care provider, while a second health care provider attempts to maintain the guide wire in the bile duct. This results in a tug-of-war caused by the alternating of the pulling of small increments of the catheter out of the channel of the endoscope and the pushing of the guide wire back into the bile duct after a catheter has been pulled.

None of the above disclosed references disclose a peel-away ERCP catheter or a method of using the same for gaining access to the pancreatic or common bile duct. Additionally, none of the above listed references disclose the use of an endoscope having a lumen, the peel-away catheter being inserted therethrough, for introducing a contrast media or a guide wire into the common bile or pancreatic ducts. Further, none of the above disclosed references teach a method for easily removing a long-line catheter from the common bile or pancreatic duct without disturbing the placement of a guide wire therein. There is a need for a method of introducing a dye, guide wire or stent into the common bile or pancreatic duct through a peel-away ERCP catheter introduced into the human body via an endoscope. There is additionally a need for a method of easily removing a catheter inserted into the common bile or pancreatic duct without disturbing the placement of a guide wire therein.

SUMMARY OF THE INVENTION

One embodiment of the present invention might include a peel-away ERCP catheter for use in introducing materials into the common bile or pancreatic ducts of the human body. An endoscope having a channel at the proximal end and an opening at the distal end and a passage therebetween is introduced into the gastroentral tract of a patient through the patient's mouth and is located such that the opening of the endoscope is adjacent the papilla of vater. A peel-away ERCP catheter including two longitudinal slits cut into the outer surface of the catheter body and additionally including two tabs connected at the proximal end of the catheter between the longitudinal slits, may be passed through the lumen of the endoscope until the distal tip of the catheter emerges from the opening of the endoscope. The distal tip of the catheter may then be guided into the ampulla of vater and into either the common bile or pancreatic duct. A guide wire may be run through the catheter and into the desired duct. The catheter may then be peeled-away from the guide wire by applying a pulling force to the tabs causing the catheter to tear along the longitudinal slits. The catheter may then be removed without disturbing the placement of the guide wire within the desired duct.

One object of the present invention is to provide a peel-away catheter having two longitudinal grooves cut into the outer surface of the catheter and two pull tabs connected between the grooves for facilitating the tearing and removal of the catheter without disturbing the placement of a guide wire therethrough.

Further objects and advantages of the present invention may be discerned by persons of ordinary skill in the art after reviewing the following written description and accompanying figures.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
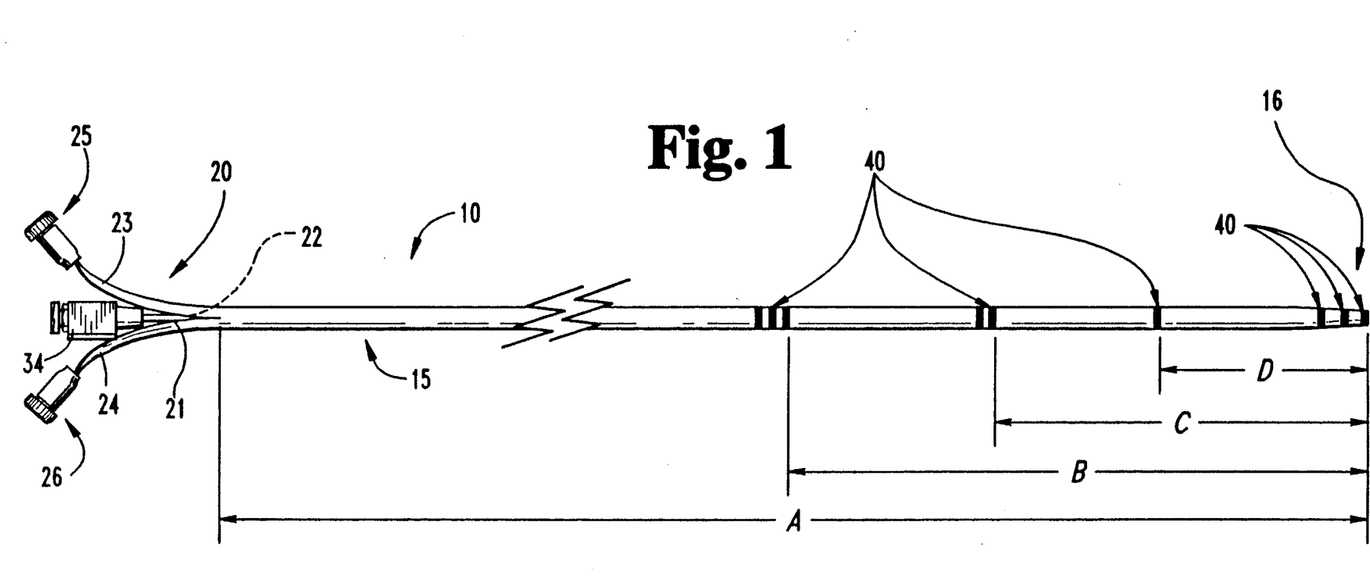
FIG. 1 is a side view of the peel-away ERCP catheter of the present invention.

A preferred embodiment of a peel-away endoscopic retrograde cholangio pancreatography (ERCP) catheter and a method for using the same are shown in FIGS. 1-8. Referring now to FIG. 1, there is shown a peel-away ERCP catheter 10 in accordance with one embodiment of the present invention. The tubular portion 15 of the peel-away catheter 10 of the present invention has approximately a uniform thickness and diameter except at its distal end 16 where there is a slight taper. The proximal end 20 of the cannula is slit longitudinally producing two open ended slits 21 and 22 at opposite sides of the tubular structure thus creating two tabs 23 and 24 which are attached to knobs 25 and 26 by being inserted between the screw 30 and 31 and socket 32 and 33 portions of the knobs, as shall be discussed further in connection with FIG. 1A.

The catheter 10 includes an introducer hub 34, having a passage therethrough, which is attached at the proximal end 20 of the catheter 10 to provide a guide for the deposit and insertion of materials through the lumen of catheter 10. Additionally, fluoroscopic stripes 40 are provided to aid in the locating and positioning of the catheter tip within the bile or pancreatic ducts. In the preferred embodiment of catheter 10 the length A of the catheter body, from the V-shaped slits to the distal tip is approximately 200 centimeters. To provide the proper perspective, length B of FIG. 1 is approximately 15 centimeters, length C is approximately 10 cm and Length D is approximately 5 cm. Additionally, as will be shown in FIG. 2, the outer surface and wall of catheter 10 of the present invention includes two longitudinal grooves 11 and 12, located on opposite sides of the tubular body 15.

Figure 1A:
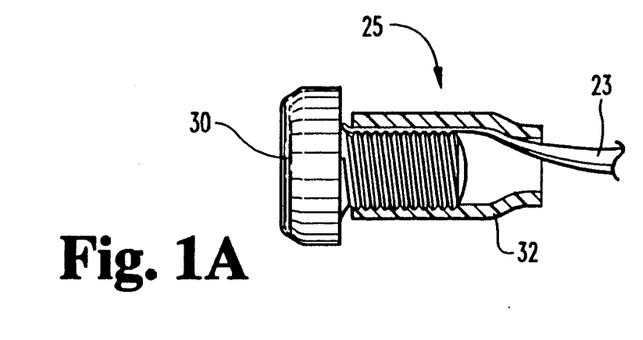
FIG. 1A is an enlarged fragmentary view of a portion of the structure of FIG. 1.

FIG. 1A is a perspective of a view showing a representative one of the tabs 23 attached to one of the knobs 25 which comprises a screw 30 and socket 32 combination. The screw 30 is screwed into the socket 32 with the end of the tab 23 in the socket. The force between the screw 30 and socket 32 maintains the end of the tab in position. The knobs 25 and 26 are used to aid in gripping the device when it is split apart.

Figure 2:
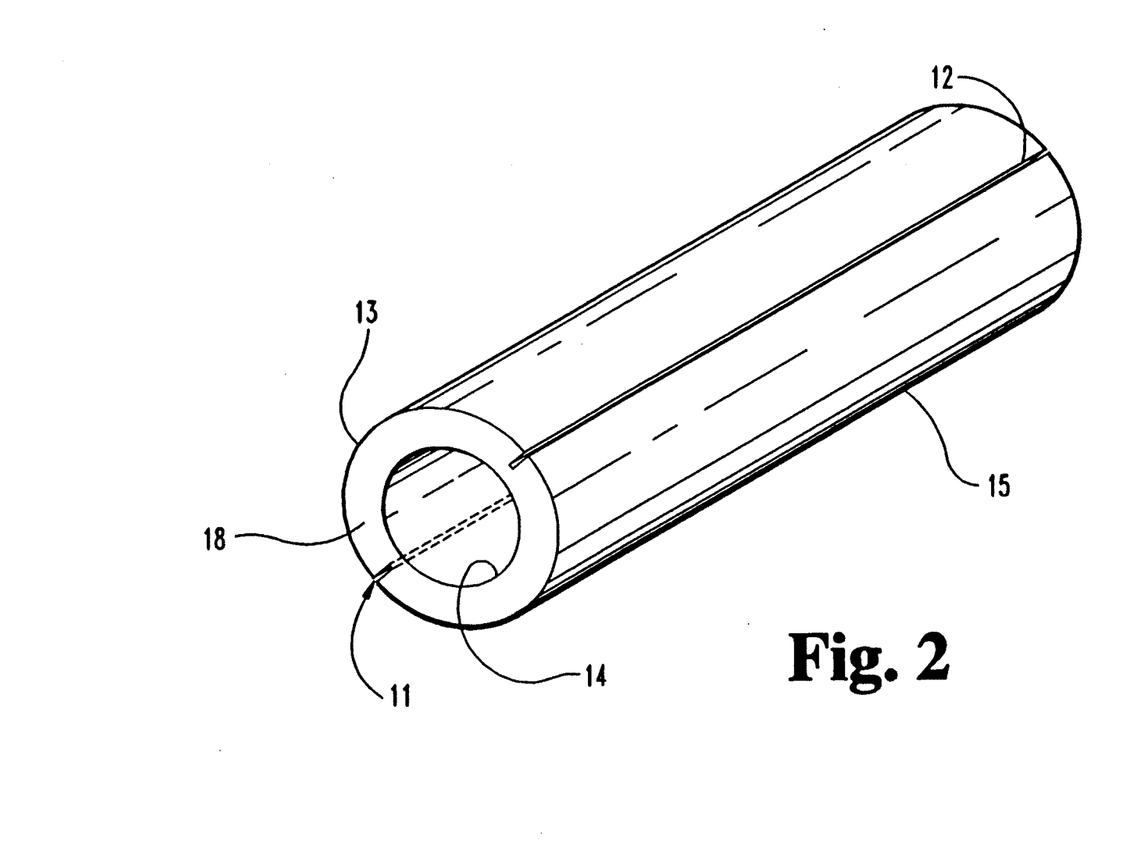
FIG. 2 is a perspective view of a portion of the tubing from which the peel-away catheter of FIG. 1 is made.

Referring now to FIG. 2, there is shown a cross-sectional portion of the tube body 15 of the peel-away catheter 10. In one preferred embodiment of the present invention, the thickness of the structure from the inner surface 14 to the outer surface 13 is 0.013 inch with a tolerance if plus or minus 0.002 inch. The total outer diameter of the catheter should be small enough to pass through the lumen of an endoscope. The outer diameter of the peel-away catheter 10 is preferably 0.072 inch with a tolerance of plus or minus 0.002 inch. Additionally, the longitudinal grooves 11 and 12 located along the outer surface 13 of the tubular body 15 of the peel-away catheter 10 are cut half way through the wall 18 of the tubular body 15. In the preferred embodiment, the longitudinal grooves 11 and 12 are 0.006 inch deep. Longitudinal grooves 11 and 12 of FIG. 2 are designed to line up with the V-cut open ended slits 21 and 22 of FIG. 1. Thus, when the knobs 25 and 26 are gripped and pulled in a direction away from the body of the catheter, the tubular body 15 will tear along the longitudinal grooves 11 and 12 resulting in two portions (70 and 71 of FIGS. 5 and 7), each of which is attached to a knob 25 or 26.

As is detailed in the Osborne patent, cited above, it is possible to cause Teflon to have a longitudinal orientation, thus facilitating longitudinal tearing of a sheath or catheter. However, it has been found that for catheters having the length necessary to extend through the gastroentral tract and into the common bile duct, the catheter must be much longer and heavier than the longitudinally oriented sheath used in connection with the vascular system, as is shown in the Osborne patent. The added length and weight of long-line catheters has been found to prevent a clean longitudinal tear down the entire length of the catheter. Rather, it has been found that attempting to tear longitudinally oriented teflon extruded to a sufficient length for a catheter of the present invention will result in non-longitudinal tearing at some point along the length of the catheter. Thus, providing longitudinal grooves along the length of the catheter is preferred to ensure that the catheter tears longitudinally down its entire length.

The catheter of FIG. 1 is made from radiopaque Teflon, the Dupont trademark for polytetraflouroethylene, which is extruded in a known fashion. The distal end of the catheter 10 is provided with a number of cylindrical marking bands 40, as shown in FIG. 1. These bands 40 are applied in any of a number of comerically known manners. The last 1 cm of the distal end 16 of the tubing is tapered. This taper aids in guiding the finished catheter through the lumen of an endoscope. After which, the tubing is cut to the desired length, which is 205 centimeters in the preferred embodiment. Additionally, the two grooves (70 and 71) are cut along the entire length of the tubing. The last five centimeters of tubing at the non-tapered end is split along the grooves 70 and 71. This results in the flaps or tabs 23 and 24 being created. These tabs 23 and 24 are then trimmed to about 2.5 cm. At this time, the introducer hub 34 is attached at the proximal end 20 of the tubing. Again, 0.039 mandrel wire is inserted into the catheter tubing, and the hub 34 is slid over the mandrel wire and into the catheter until the hub is flush with the bottom of the V-shaped open ended slits 21 and 22. The mandrel wire is then removed. Finally, 14 Fr. duodenal tubing is placed over the end of each tab 23 and 24 and a plastic thumbscrew is inserted into the tubing, as is illustrated in connection with FIG. 1A. In the preferred embodiment, the catheter is sterilized and packaged with a sterilized stylet wire in a hermetically sealed package.

Figure 3:
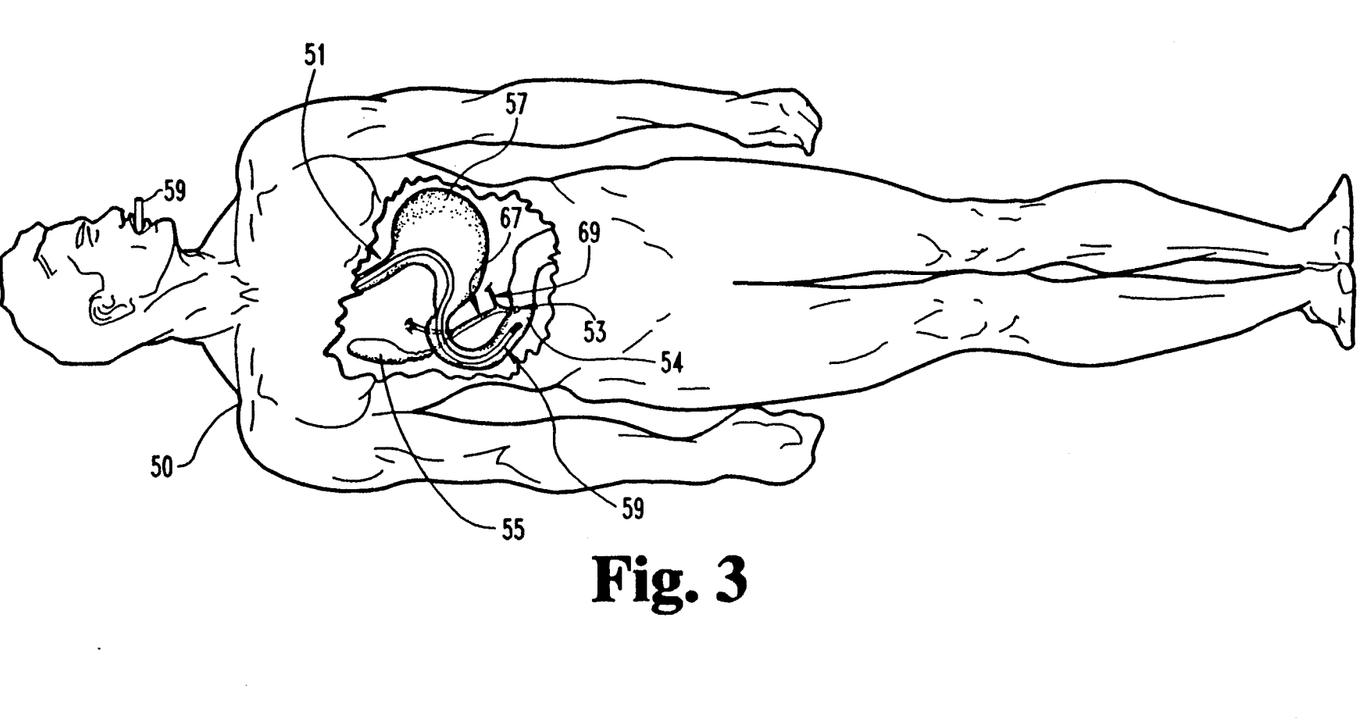
FIG. 3 is a top view of a human showing the insertion of an endoscope into the mouth of a patient with the distal end of the endoscope being brought into close proximity with the papilla of vater which leads to the common bile and pancreatic ducts.

A method for using the peel-away ERCP catheter of the preferred embodiment will now be explained in connection with FIGS. 3-7. Referring now to FIG. 3, there is shown a top explanatory view showing the insertion of an endoscope into a human body. In the present invention, an endoscope 59 has been inserted into the mouth of the patient 50 and guided down the esophagus 51, through the stomach 57 and into the duodenum 54. The endoscope 59 of the present invention has a passage, or lumen, running longitudinally through the endoscope beginning from a channel located through the proximal end of the endoscope and terminating at an opening 65 at the distal end of the endoscope.

The endoscope is guided into the duodenum 54 until the opening 65 is in close proximity to the papilla of vater 53, located between the sphincter of Oddi 61, which leads to the to the common bile duct 67 and the pancreatic duct 69. The channel at the proximal end of the endoscope 59 remains outside the mouth of the patient 50.

Figure 4A:
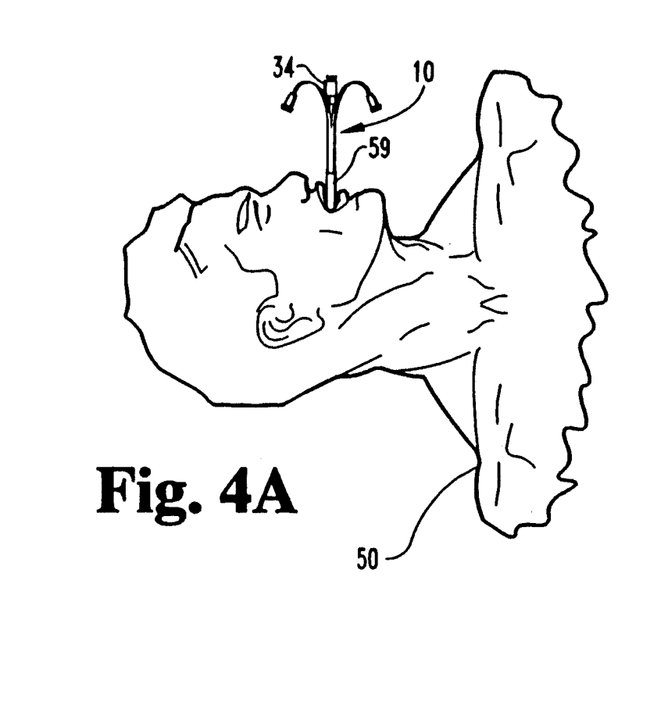
FIG. 4A is a view of the peel-away catheter of the present invention after being inserted through the lumen of the endoscope of FIG. 3.
Figure 4B:
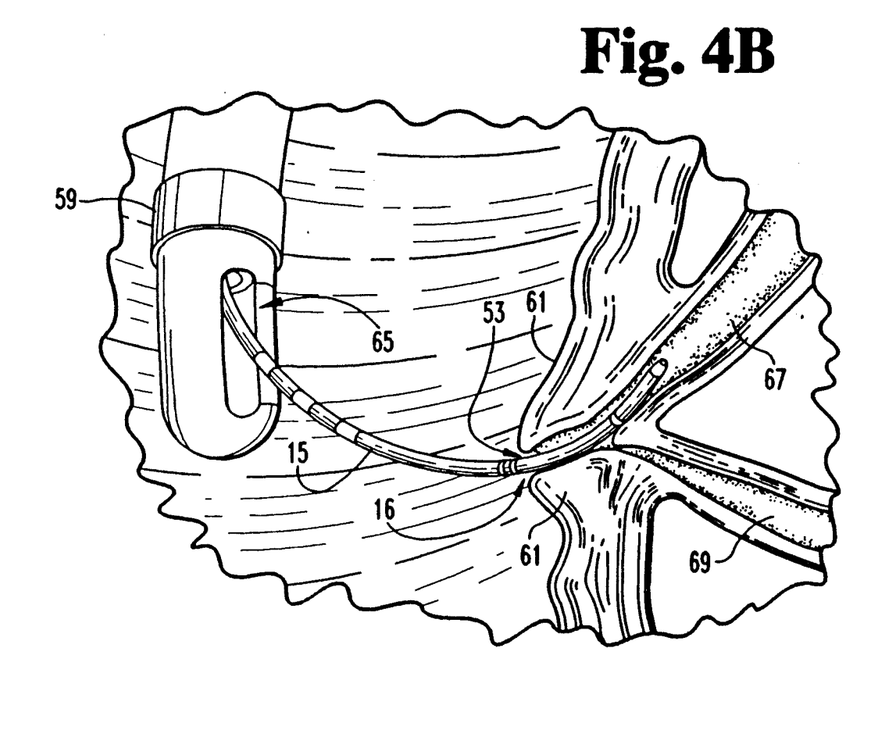
FIG. 4B is an enlarged view of the distal end of the peel-away catheter, shown exiting an opening in the distal end of the endoscope, which has been inserted into the common bile duct.

In accordance with one method of use of the catheter of the present invention, once the endoscope is in proper position, a peel-away ERCP catheter having an outer diameter smaller than the inner diameter of the endoscope lumen, is inserted into the proximal opening of endoscope 59 (FIG. 4A) and is passed through the lumen of the endoscope until the tapered tip at the distal end 16 of the catheter emerges from the opening 65 at the distal end of the endoscope. The outer diameter of the peel-away catheter is designed to be 5.5 French in one preferred embodiment so as to move freely through the endoscope. Additionally, the distal tip of the catheter 10 may be guided between through the papilliary orifice of the papilla of vater 53, adjacent the sphincter of oddi 61 and into the common bile duct 67, as is shown in FIG. 4B. After the distal end 16 of the catheter 10 is in position in the common bile duct 67, it is possible to inject a contrast media, such as a radiopaque dye, into the bile duct.

Figure 5A:
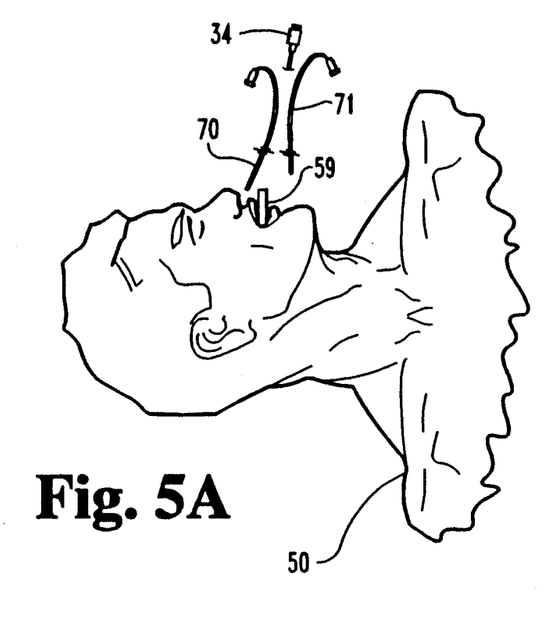
FIG. 5A shows the peel-away catheter after it has been peeled away and removed from the lumen of the endoscope.
Figure 5B:
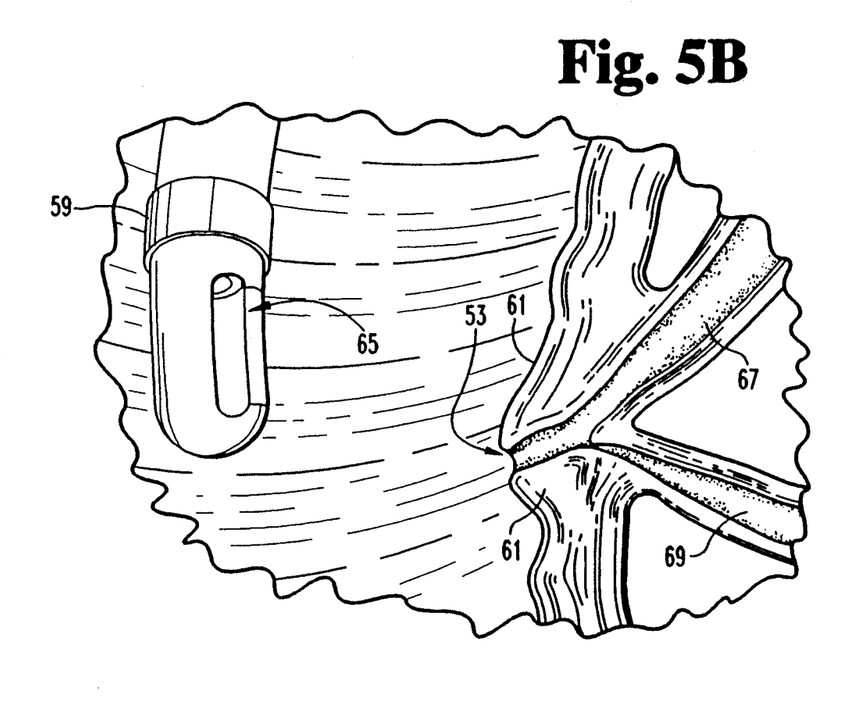
FIG. 5B shows the tip of the endoscope and papilla of vater after the catheter of FIG. 4B has been peeled-away and removed from the papilliary orifice.

After the contrast media has been injected into the common bile duct the catheter may be removed from the endoscope as is shown in FIGS. 5A and 5B. A healthcare provider may remove the catheter by gripping the knobs of the peel-away catheter 10 and pulling them apart or in a downward direction. The resulting force on the knobs causes the catheter to tear along the longitudinal grooves while simultaneously pulling the catheter from the channel of the endoscope 59, FIG. 5B. Additionally, the catheter body is torn into two separate halves 70 and 71, and the introducer hub 34 can now be removed.

Figure 6A:
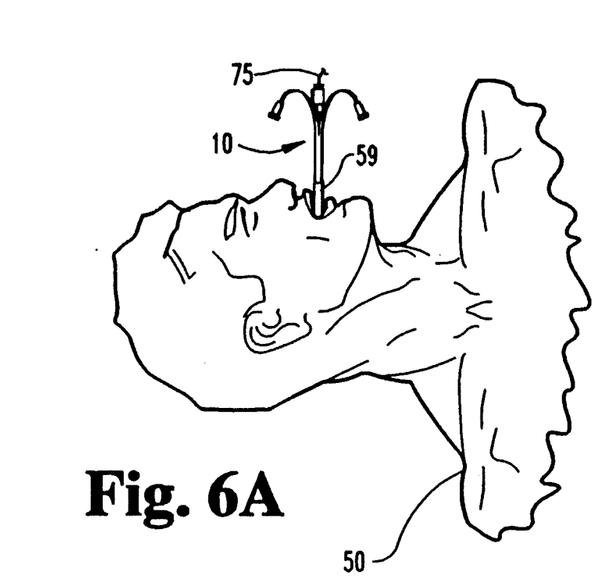
FIG. 6A shows the peel-away catheter of the present invention having a guide wire therethrough.
Figure 6B:
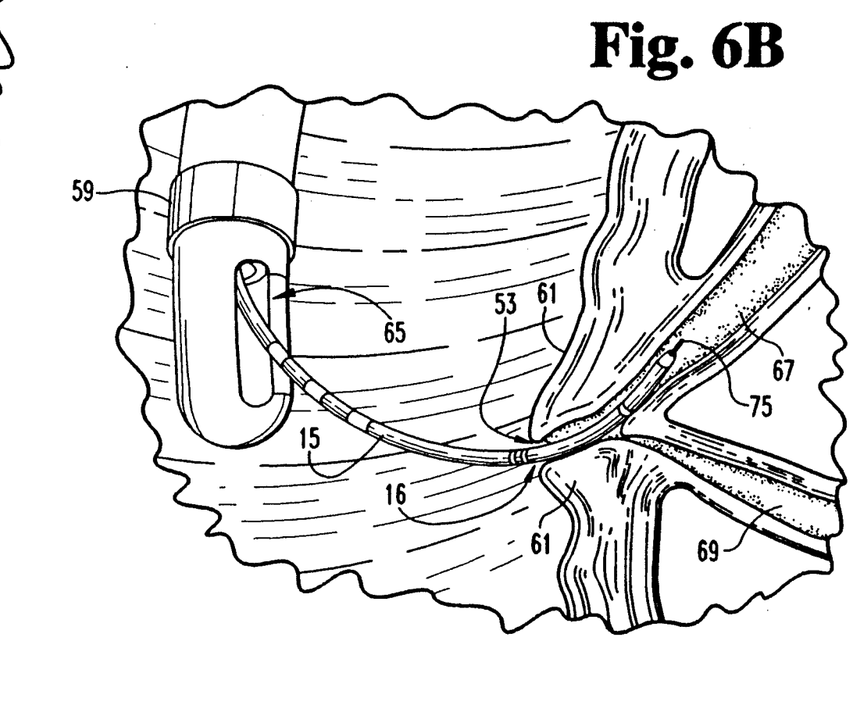
FIG. 6B shows the guide wire protruding from the distal end of the peel-away catheter located within the common bile duct of a human body.

Additionally, once the peel-away ERCP catheter of the present invention has been inserted into the bile duct, through the endoscope 59, a guide wire may be passed through the catheter 10 into the common bile duct 67, as shown in FIGS. 6A and 6B. The guide wire 75 is inserted into the introducer hub 34 and is then run through the tubular body 15 where it exits the distal end 16 of the catheter into the common bile duct 67.

Figure 7A:
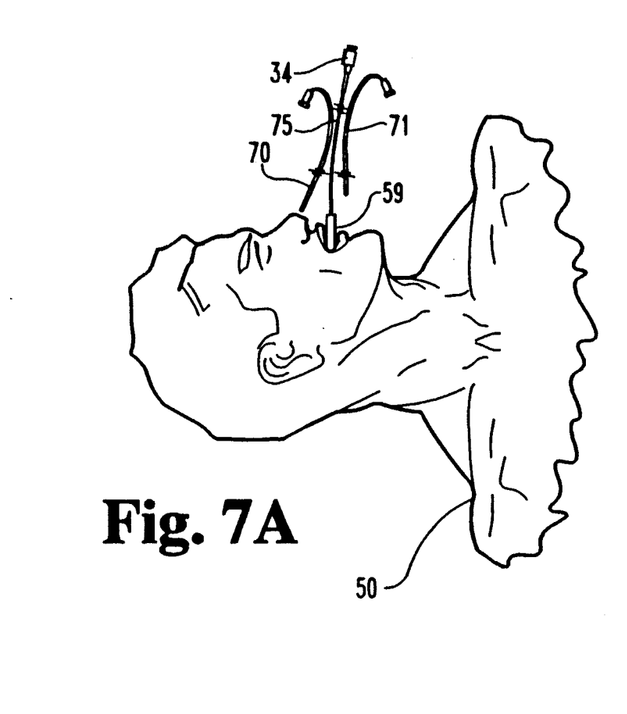
FIG. 7A shows the peeling away and removal of the peel-away catheter which leaves the guide wire of FIG. 6B positioned within the common bile duct.
Figure 7B:
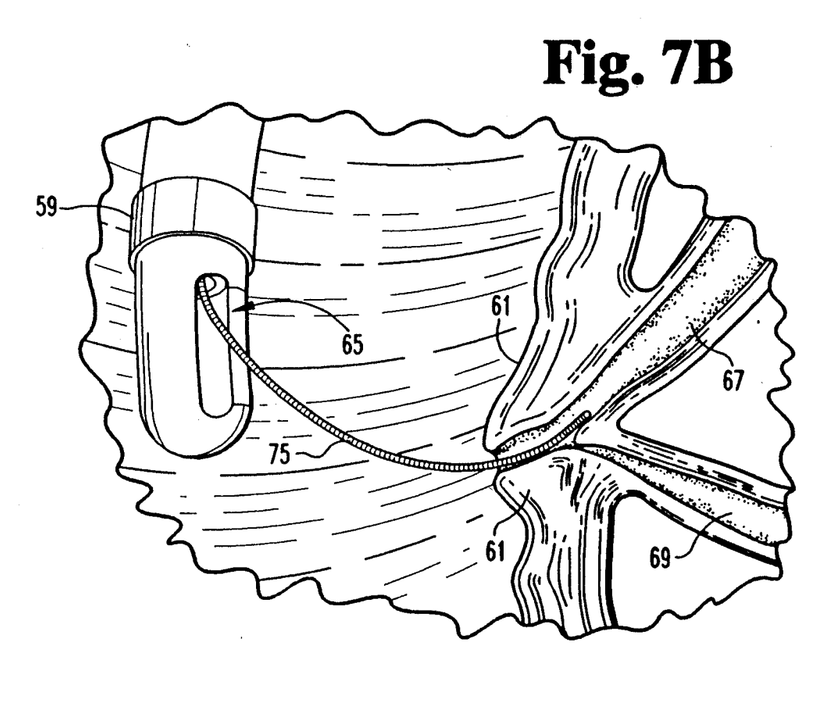
FIG. 7B shows the guide wire positioned within the common bile duct.

Referring now to FIGS. 7A and 7B, the catheter may be easily removed in the same manner as explained in connection with FIGS. 5A and 5B, without disturbing the placement of the guide wire 75 within the bile duct 67. A healthcare provider need only hold the wire at the channel of the endoscope while a second person peels the catheter away from the guide wire 75. Thus, the guide wire does not move when the catheter is removed from the patient 50. Additionally, peeling the catheter away from the guide wire results in much less friction on the wire than is produced using unsplit catheters, so that the guide wire is more likely to remain in the common bile duct 67 without employing the pushing and pulling technique, described above, for keeping the guide wire within the common bile duct 67. The introducer hub 34 is then slid off of the guide wire at the proximal end of the wire.

Figure 8A:
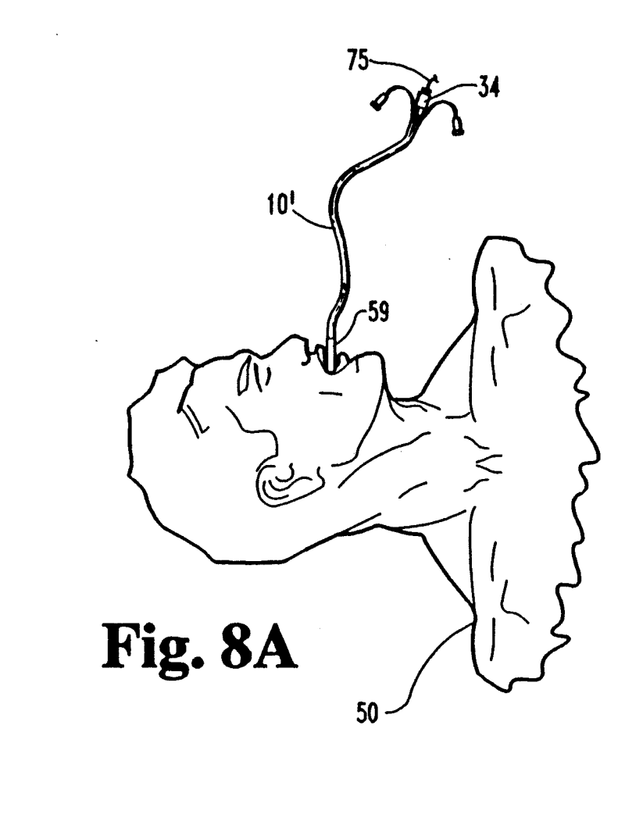
FIG. 8A shows the introduction of a second peel-away catheter over the guide wire located within the endoscope of FIG. 3.
Figure 8B:
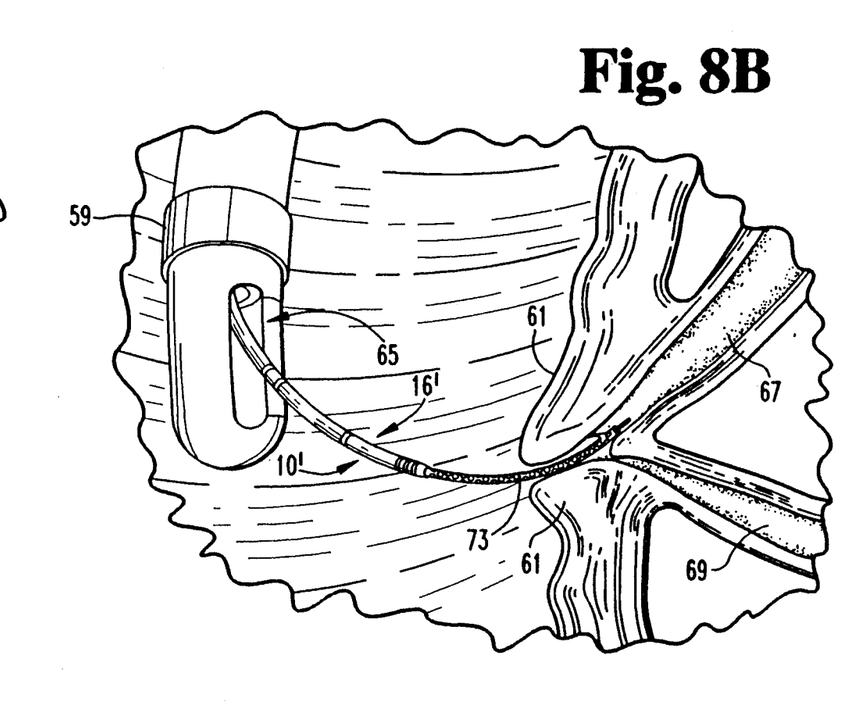
FIG. 8B shows a stent being pushed by a peel-away catheter along a guide wire, the distal end of the guide wire being located within the common bile duct.

Additionally, once the guide wire has been placed into the common bile duct 67 (or in the pancreatic duct 69) and the first peel-away catheter has been peeled and removed, it may be desirable to place a stent into the common bile or pancreatic duct. As such, an indwelling stent, such as that shown in U.S. Pat. No. 5,052,998, that document incorporated herein by reference, may be placed over the guide wire 75 and pushed into the desired duct using a second catheter, which is additionally run over the guide wire 75. FIG. 8A shows the introduction of a second catheter 10' into the channel of the endoscope 59. The second catheter 10' may be run over the guide wire 75 located through the lumen of the endoscope and present within the common bile or pancreatic duct. Additionally, FIG. 8B shows the distal end 16' of the catheter 10' used to push a biliary stent 73 along the guide wire 75 and into the common bile duct. Once the stent is in place, the second catheter and the guide wire 75 may be removed simultaneously without peeling the catheter away or the catheter 10' may be peeled-away, leaving the guide wire in place. This second catheter may be a regular 320 cm, 6 Fr., catheter, if the guide wire is to be removed with the catheter, or it may be a second peel-away catheter in accordance with the present invention. The peel-away nature of the catheter of the present invention prevents the difficulties in maintaining the guide wire 75 within the bile or pancreatic duct found in the prior systems.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of removing a tearable catheter from a duct, comprising the steps of:
    (a) inserting an endoscope into the mouth of a patient, said endoscope including a channel at a proximal end of said endoscope and an opening at the distal end of said endoscope and additionally including a passage therebetween;
    (b) guiding said endoscope through the gastroentral tract of said patient until said opening is in close proximity to the papilla of vater located within the wall of said patient's duodenum;
    (c) guiding a tearable catheter through said passage of said endoscope until a distal end of said catheter emerges from said opening, said tearable catheter including two longitudinal grooves cut along a body of said catheter from the distal end of said catheter to a proximal end of said catheter, said proximal end of said catheter additionally including two tabs connected between said two grooves;
    (d) guiding said distal end of said catheter into a duct; and
    (e) tearing said catheter by applying a pulling force on said two tabs while simultaneously removing said catheter from said passage of said endoscope.

2. The method of removing a tearable catheter of claim 1, comprising the step of:
    (f) injecting a radiopaque dye through said catheter and into said duct prior to tearing and removing said catheter.

3. The method of removing a tearable catheter of claim 1, comprising the steps of:

(g) before tearing said catheter in step (e), guiding a guide wire through said tearable catheter until the distal end of said guide wire emerges from the distal end of said catheter into said duct; and (h) holding the proximal end of said guide wire while tearing and removing said catheter to prevent said guide wire from being removed from said duct.

4. The method of removing a tearable catheter of claim 3 additionally comprising the steps of:

(i) placing a stent over the proximal end of said guide wire, the distal end of said guidewire being located within said duct;

(j) placing a second tearable catheter over said distal end of said guide wire after said stent has been placed;

(k) pushing said stent into said duct using said second tearable catheter; and (l) tearing and removing said second tearable catheter from said endoscope while holding said proximal end of said guide wire to prevent said guide wire from being removed from said duct.

5. The method of removing a tearable catheter of claim 1, wherein said duct is the pancreatic duct.

6. The method of removing a tearable catheter of claim 1, wherein said duct is the common bile duct.

7. A medical device for introducing a guide wire into a common bile duct, comprising:

an endoscope which may be inserted through the gastroentral tract of a human body, said endoscope including a channel at a proximal end of said endoscope and an opening at a distal end of said endoscope and additionally including a passage therebetween;

a tearable catheter, located through said endoscope passage, a distal tip of said catheter emerging from said opening of said endoscope and being guided into a common bile duct of said human body, said catheter comprising:

a plurality of longitudinal grooves cut in at least two sides of said catheter;

a plurality of pull tabs connected between said grooves to facilitate the tearing of said catheter along said longitudinal grooves and for aiding in the removal of said catheter without disturbing the placement of a guide wire therethrough; and a guide wire, located through a lumen of said catheter, a distal end of said guide wire extending from said distal end of said catheter into said common bile duct and a proximal end of said guide wire extending from a proximal end of said catheter and said endoscope to facilitate the introduction of material passed over said guide wire into said common bile duct.

8. The medical device for introducing a guide wire into a common bile duct of claim 7, additionally comprising a plurality of knobs connected to the proximal ends of said pull tabs, one knob connected per pull tab, to initially facilitate the tearing of said catheter along said longitudinal grooves.

9. A method of removing a tearable catheter from a duct, comprising the steps of:

(a) inserting an endoscope into a patient, said endoscope including a channel at a proximal end of said endoscope and an opening at the distal end of said endoscope and additionally including a passage therebetween;

(b) guiding said endoscope through said patient until said opening is in close proximity to a duct;

(c) guiding a tearable catheter through said passage of said endoscope until a distal end of said catheter emerges from said opening, said tearable catheter including two longitudinal grooves cut along a body of said catheter from the distal end of said catheter to a proximal end of said catheter, the proximal end of said catheter additionally including two pull tabs connected between said two grooves;

(d) guiding said distal end of said catheter into said duct; and (e) tearing said catheter by applying a pulling force on said two tabs while simultaneously removing said catheter from said passage of said endoscope.

10. The method of removing a tearable catheter of claim 9, comprising the steps of:

(f) before tearing said catheter in step (e), guiding a guide wire through said tearable catheter until a distal end of said guide wire emerges from a distal end of said catheter into said duct; and (g) holding a proximal end of said guide wire while tearing and removing said catheter to prevent said guide wire from being removed from said duct.

11. The method of removing a tearable catheter of claim 10 additionally comprising the steps of:

(i) placing a stent over the proximal end of said guide wire, the distal end of which is located within said duct;

(j) placing a second tearable catheter over said distal end of said guide wire after said stent has been placed;

(k) pushing said stent into said duct using said second tearable catheter; and (l) tearing and removing said second tearable catheter from said endoscope while holding said proximal end of said guide wire to prevent said guide wire from being removed from said duct.

12. The method of removing a tearable catheter of claim 11, wherein said duct is the pancreatic duct.

13. The method of removing a tearable catheter of claim 11, wherein said duct is the common bile duct.

* * * * *

UNITED STATES PATENT AND TRADEMARK OFFICE
CERTIFICATE OF CORRECTION

PATENT NO. : 5,320,602

DATED : June 14, 1994

INVENTOR(S) : John Karpiel

It is certified that error appears in the above-identified patent and that said Letters Patent is hereby corrected as shown below:

Column 9, line 1, "(g)" should be changed to "(f)";

Column 9, line 5, "(h)" should be changed to "(g)";

Column 9, line 10, "(i)" should be changed to "(h)";

Column 9, line 13, "(j)" should be changed to "(i)";

Column 9, line 16, "(k)" should be changed to "(j)";

Column 9, line 18, "(l)" should be changed to "(k)".

Column 10, line 39, "(i)" should be changed to "(h)";

Column 10, line 42, "(j)" should be changed to "(i)";

Column 10, line 45, "(k)" should be changed to "(j)";

Column 10, line 47, "(l)" should be changed to "(k)".

Signed and Sealed this

Thirtieth Day of May, 1995

Attest:

BRUCE LEHMAN

Attesting Officer

Commissioner of Patents and Trademarks